(12) United States Patent
Koehler

(10) Patent No.: US 8,388,550 B2
(45) Date of Patent: Mar. 5, 2013

(54) GUIDABLE CUTTING INSTRUMENT

(75) Inventor: Cleve Koehler, Ellettsville, IN (US)

(73) Assignee: Cook Medical Technologies LLC, Bloomington, IN (US)

( * ) Notice: Subject to any disclaimer, the term of this patent is extended or adjusted under 35 U.S.C. 154(b) by 301 days.

(21) Appl. No.: 12/468,306

(22) Filed: May 19, 2009

(65) Prior Publication Data

US 2010/0298737 A1 Nov. 25, 2010

(51) Int. Cl.
*A61B 10/00* (2006.01)
*A61B 17/32* (2006.01)
*A61B 17/58* (2006.01)
*A61B 17/60* (2006.01)
*A61F 2/00* (2006.01)

(52) U.S. Cl. ............ 600/567; 606/171; 604/95.01

(58) Field of Classification Search ......... 600/566, 600/567, 564, 568; 606/170, 171; 604/95.01
See application file for complete search history.

(56) References Cited

U.S. PATENT DOCUMENTS

| | | | |
|---|---|---|---|
| 3,342,175 A | 9/1967 | Bulloch | |
| 3,584,624 A * | 6/1971 | de Ciutiis | 604/170.01 |
| 4,911,148 A | 3/1990 | Sosnowski et al. | 128/6 |
| 4,945,920 A | 8/1990 | Clossick | 128/751 |
| 4,958,625 A | 9/1990 | Bates et al. | 128/754 |
| 5,095,910 A * | 3/1992 | Powers | 600/461 |
| 5,152,749 A | 10/1992 | Giesy et al. | 604/164 |
| 5,195,533 A | 3/1993 | Chin et al. | 128/754 |
| 5,313,958 A | 5/1994 | Bauer | 128/754 |
| 5,318,528 A * | 6/1994 | Heaven et al. | 604/95.01 |
| 5,538,010 A | 7/1996 | Darr et al. | 600/567 |
| 5,916,175 A | 6/1999 | Bauer | 600/567 |
| 5,951,489 A | 9/1999 | Bauer | 600/567 |
| 5,968,059 A | 10/1999 | Ellis et al. | 606/167 |
| 5,989,196 A | 11/1999 | Chu et al. | 600/567 |
| 6,024,703 A * | 2/2000 | Zanelli et al. | 600/437 |
| 6,126,633 A | 10/2000 | Kaji et al. | 604/95.04 |
| 6,425,887 B1 | 7/2002 | McGuckin et al. | 604/272 |
| 6,595,958 B1 | 7/2003 | Mickley | 604/164.01 |
| 7,018,343 B2 | 3/2006 | Plishka | 600/564 |
| 7,282,020 B2 | 10/2007 | Kaplan | 600/7 |
| 7,704,234 B2 * | 4/2010 | Darr | 604/164.01 |
| 2004/0133124 A1 * | 7/2004 | Bates et al. | 600/564 |
| 2004/0133168 A1 | 7/2004 | Salcudean et al. | 604/164.13 |
| 2004/0210209 A1 | 10/2004 | Yeung et al. | 604/500 |
| 2006/0064062 A1 | 3/2006 | Gurusamy et al. | 604/170.03 |
| 2007/0198043 A1 | 8/2007 | Cox et al. | 606/185 |

FOREIGN PATENT DOCUMENTS

| | | |
|---|---|---|
| JP | 9-084747 | 3/1997 |
| JP | 2001-190555 A | 7/2001 |

* cited by examiner

FOREIGN PATENT DOCUMENTS

*Primary Examiner* — Max Hindenburg
*Assistant Examiner* — John Pani
(74) *Attorney, Agent, or Firm* — Brinks Hofer Gilson & Lione

(57) ABSTRACT

A guidable cutting instrument for cutting a tissue specimen from a tissue mass comprises a cannula having a curve formed along a distal portion thereof, and a stylet having a specimen-receiving notch and a curve formed along a distal portion thereof. The stylet is received in the cannula, and is axially extendable therefrom such that the notch is capable of penetrating the tissue mass. The cannula is axially movable over the extended stylet for severing the specimen from the mass for capture in the notch. The cannula and stylet are each structured and arranged for relative rotation between a first position wherein the cannula curve and the stylet curve are in phase to define a curved condition for a length of the cutting instrument, and a second position wherein the cannula curve or stylet curve is rotated relative to the other curve in a manner to define a generally linear condition of the cutting instrument. The selective relative curvature allows the cutting instrument to be steered around obstructions encountered in the body under real time visualization.

13 Claims, 4 Drawing Sheets

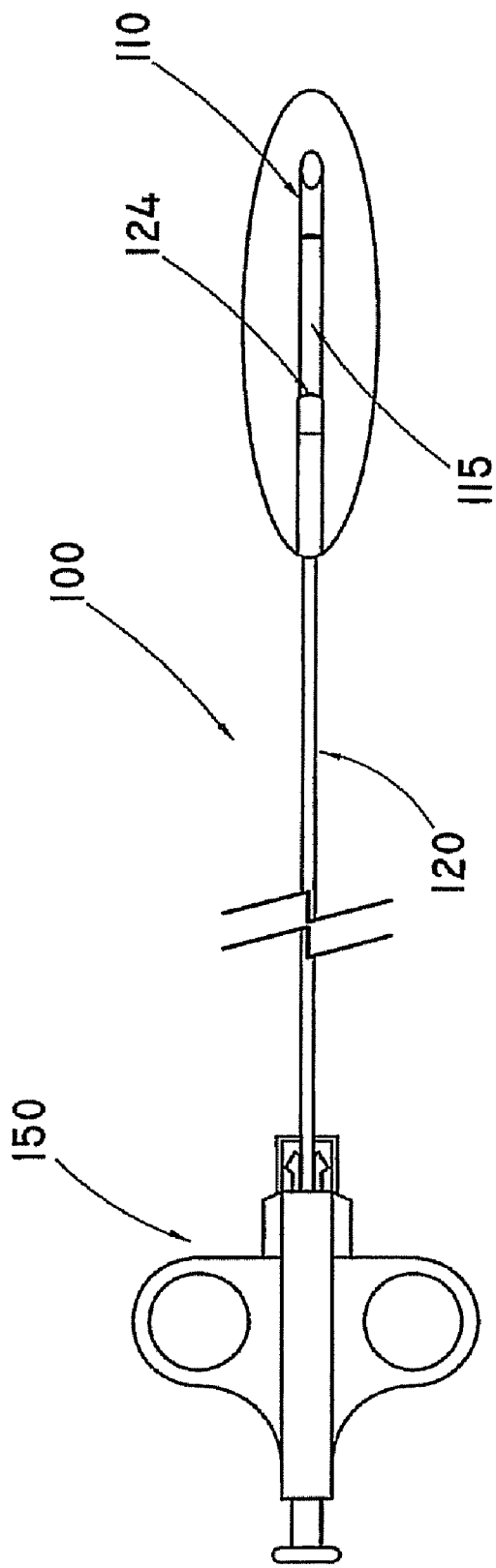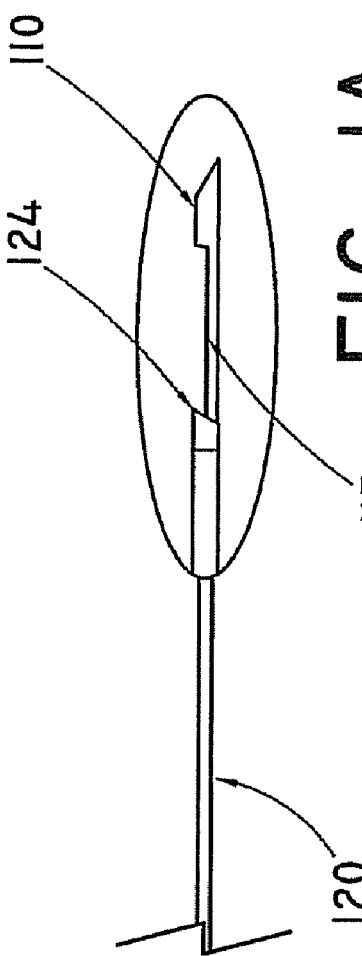
FIG. 1 PRIOR ART
FIG. 1A PRIOR ART

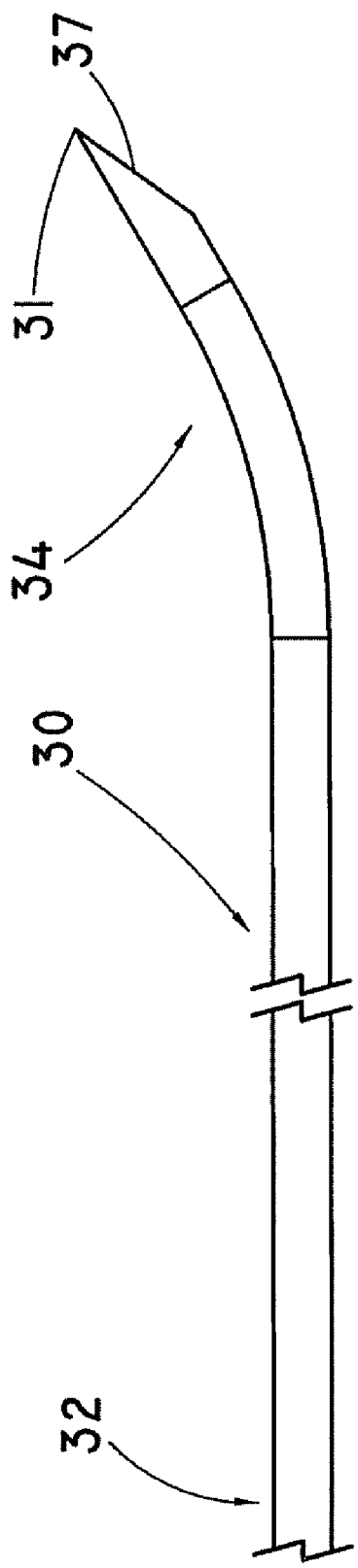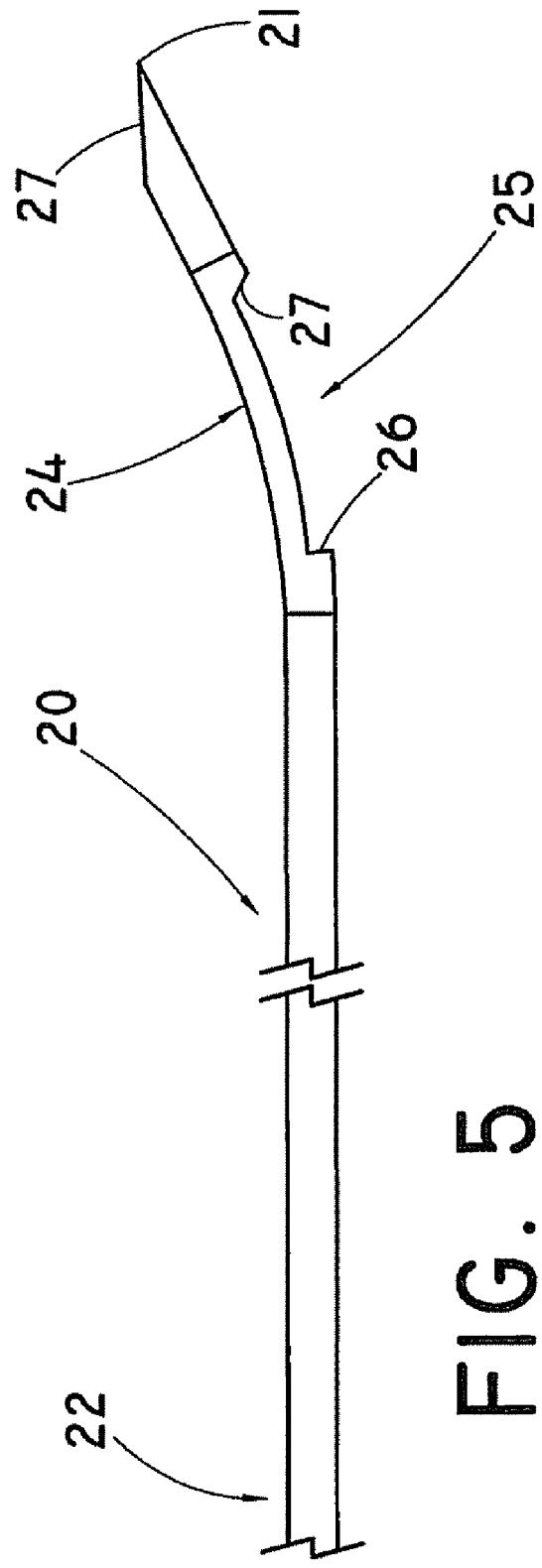

GUIDABLE CUTTING INSTRUMENT

BACKGROUND OF THE INVENTION

1. Technical Field

The present invention relates to a guidable cutting instrument, and more particularly, to a guidable needle for use in biopsy sampling of tissue.

2. Background Information

Biopsy is the removal and study of body tissue for medical diagnosis. Typically, physicians obtain biopsy samples in order to detect tissue abnormalities, such as the presence of a cancerous growth, and/or to determine the extent to which the cancerous growth may have spread in the affected tissue. Various known biopsy instruments may be used to acquire tissue samples from different areas of interest in the body of a patient.

Biopsy instruments often comprise a two-part needle assembly comprising a stylet and cannula. One example of a conventional biopsy instrument is the QUICK-CORE® Biopsy Needle, available from Cook Incorporated, of Bloomington, Ind. The QUICK-CORE® needle 100 is shown in FIGS. 1-1A. Needle 100 includes a stylet 110 and an outer cannula 120 enclosing the stylet. Stylet 110 has a tissue collecting or specimen notch 115 formed near the distal end of the stylet. Cannula 120 has a sharpened point 124 at its distal end. The stylet 110 and the cannula 120 are arranged so that the cannula point 124 is advanceable over the stylet 110 in order to cover the specimen notch 115.

Two-part biopsy needles having respective inner and outer members, such as stylet 110 and cannula 120, are now well-known in the medical community. In use, such needles may be activated by a spring-loaded handle 150 of a type disclosed, e.g., in U.S. Pat. No. 5,538,010. Activation of the spring-loaded handle 150 causes rapid forward movement of the cannula 120 over the stylet 110, and in particular, over the stylet notch 115. This action severs a specimen of the prolapsed tissue into which the needle has been inserted, which specimen becomes retained in the specimen notch 115 of the stylet 110. Once the biopsy needle 100 is withdrawn, the cannula is retracted, and the tissue sample may be recovered from the stylet for further examination.

This prior art needle assembly works very well for a variety of biopsy procedures. However, the ability of the needle to negotiate through curves in the vasculature, and particularly, the ability of the needle to avoid body structures and organs situated in the path of the needle, is limited. As a result, use of the prior art assembly is generally limited to a "straight shot" type of procedure, in which the needle is inserted percutaneously and directly advanced in generally linear fashion to a target lesion that is accessible without significant obstruction.

In recent years, techniques for medical imagery have improved to an extent that physicians are now able to clearly view the positioning of a medical interventional device as it advances along a designated pathway within the body of a patient. Newer imaging techniques are capable of providing detail that is superior to that provided by many classical techniques, such as x-ray. For example, medical ultrasonography enables the physician to view a sonogram in real time that clearly shows the position of a device, such as a needle, as it advances through the body. This ability to view the position of a medical device within the body of a patient in real time provides the physician with the opportunity to manipulate the position of the device as it navigates the designated pathway. However, "straight shot" type devices are in large part incapable of being steered, navigated, or otherwise bended around a body organ or other obstruction that may be encountered within the body of the patient.

It would be desirable to provide a cutting device, such as a biopsy tissue-sampling needle, that is capable of effectively negotiating around body organs or other obstructions in the body of a patient. It would also be desirable to provide a cutting instrument of relatively simple design that enables the physician to obtain a tissue sample from a remote target site within the body of the patient in a manner that does not require passing the cutting instrument through obstructions that may be encountered along the pathway.

BRIEF SUMMARY

The foregoing problems are solved and a technical advantage is achieved by the present invention. In one form thereof, the invention comprises a guidable cutting instrument for use in cutting a tissue specimen from a tissue mass. The cutting instrument includes a cannula having a proximal portion and a distal portion, the distal portion having a curve formed therealong; and a stylet having a proximal portion and a distal portion, the stylet distal portion having a specimen-receiving notch formed therein and having a curve formed therealong. The stylet is received in the cannula and axially extendable therefrom, such that the notch is capable of penetrating the tissue mass. The cannula is axially movable over the extended stylet for severing the tissue specimen from the mass for capture in the notch. The cannula and stylet are structured and arranged for relative rotation between a first position wherein the cannula curve and the stylet curve are in phase and the respective curves coincide to define a curved condition for a length of the cutting instrument, and a second position wherein one of the cannula curve and stylet curve is rotated relative to the other curve in a manner to define a generally linear condition of the cutting instrument.

In another form thereof, the invention comprises a method of retrieving a tissue specimen from a tissue mass of a patient. A tissue-penetrating cutting instrument is provided. The cutting instrument includes a cannula having a proximal portion and a distal portion, wherein the distal portion has a curve formed therealong; and a stylet having a proximal portion and a distal portion, wherein the stylet distal portion has a specimen-receiving notch formed therein and has a curve formed therealong. The stylet is received in the cannula, and is axially extendable therefrom, and the cannula is axially extendable over said extended stylet. The cannula and stylet are structured and arranged for relative rotation therebetween from a first position wherein the cannula curve and the stylet curve are in phase and the respective curves coincide to define a curved condition for a distal portion of the cuffing instrument, and a second position wherein one of the curves is rotated relative to the other curve to define a generally linear condition of the cutting instrument. A distal end of the tissue-penetrating cutting instrument is inserted into an interior space of the body of the patient, and the interior space is navigated under real time visualization such that the cutting instrument distal end approaches the tissue mass. The stylet is advanced such that the notch extends beyond the cannula, and penetrates the tissue mass. The cannula is advanced over the notch to sever the specimen from the tissue mass, and to capture the severed specimen in the notch. The cutting instrument is thereafter withdrawn, and the specimen is retrieved from the notch for examination.

BRIEF DESCRIPTION OF THE DRAWINGS

FIG. 1 illustrates a prior art biopsy cutting instrument, showing an enlarged view of the distal portion of the cutting instrument;

FIG. 1A is a side view of the distal portion of the cutting instrument of FIG. 1A, rotated 90 degrees from the view of FIG. 1;

FIG. 4 is a side view of the curved outer cannula of the needle assembly portion of the guidable cutting instrument of FIG. 2; and FIG. 5 is a side view of the curved inner stylet of the needle assembly portion of the guidable cutting instrument of FIG. 2.

DETAILED DESCRIPTION OF THE PREFERRED EMBODIMENTS

Figure 2:
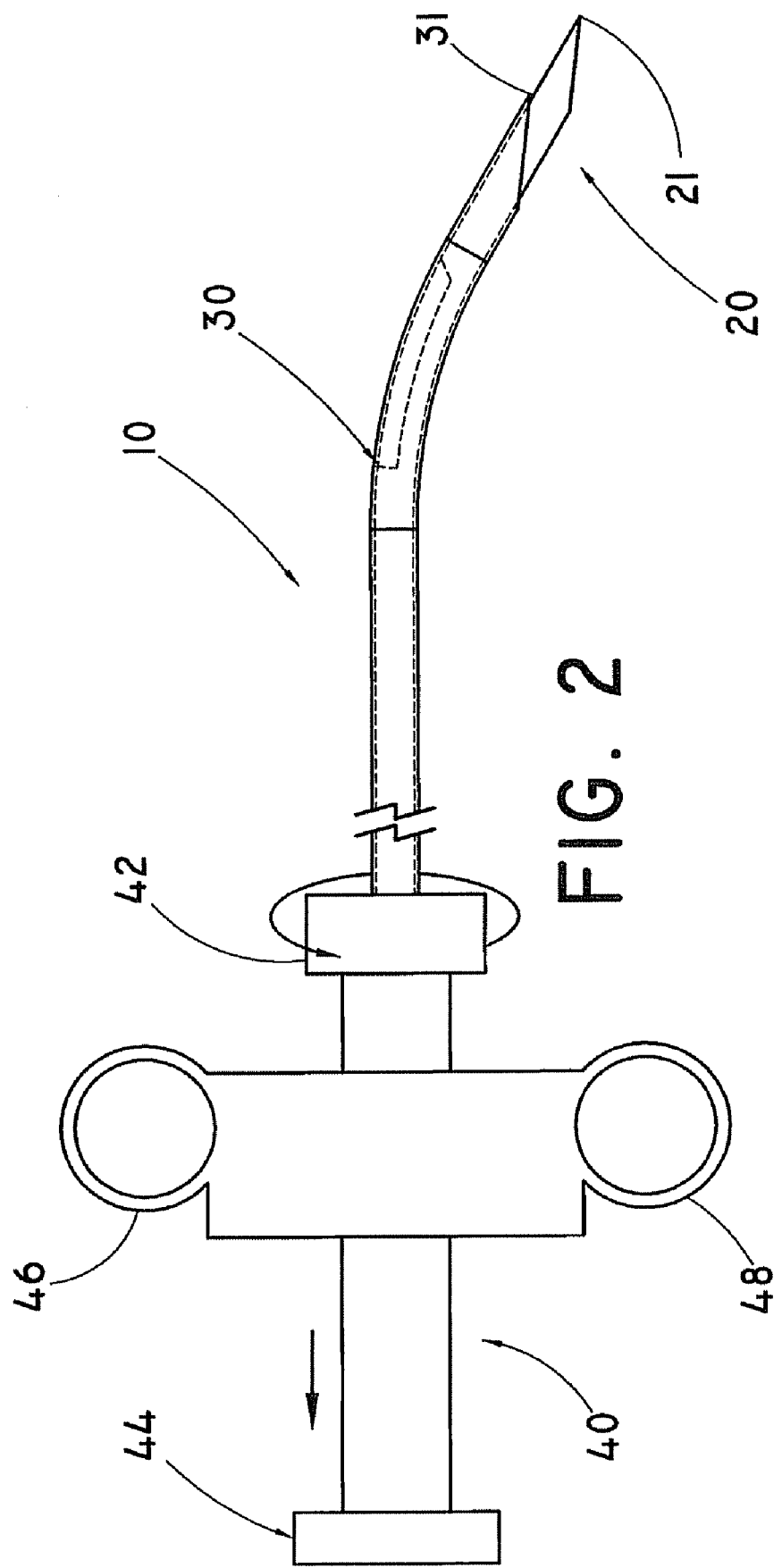
FIG. 2 is a plan view of one embodiment of an inventive guidable surgical cutting instrument, wherein the respective stylet and outer cannula are oriented in phase, resulting in the curvature of the distal end of the cutting instrument.

For purposes of promoting an understanding of the present invention, reference will now be made to the embodiments illustrated in the drawings, and specific language will be used to describe the same. It should nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

In the following discussion, the terms "proximal" and "distal" will be used to describe the opposing axial portions of the inventive cutting instrument, as well as the axial portions of various component features. The term "proximal" is used in its conventional sense to refer to the portion of the cutting instrument (or component thereof) that is closest to the operator during use of the cutting instrument. The term "distal" is used in its conventional sense to refer to the portion of the cutting instrument (or component thereof) that is initially inserted into the patient, or that is closest to the patient during use.

Generally speaking, the present invention is directed to a guidable cutting instrument. The guidable cutting instrument may be used to excise a sample of tissue from a patient for a purpose, e.g., of performing a biopsy on the excised tissue sample. FIG. 2 illustrates a plan view of one embodiment of an inventive guidable cutting instrument 10. In the embodiment shown, guidable cutting instrument 10 includes an outer cannula 30, a tissue penetrating stylet 20 disposed within an inner passageway of the outer cannula, and a handle mechanism 40. Only the distal tip portion 21 of stylet 20 that extends axially beyond the distal tip 31 of the cannula 30 is visible in this figure. In the view depicted in FIG. 2, the respective distal ends of the stylet 20 and the outer cannula 30 are "in phase", as further described herein. This arrangement results in the distal end of cutting instrument 10 having the curved configuration shown in the figure.

Figure 3:
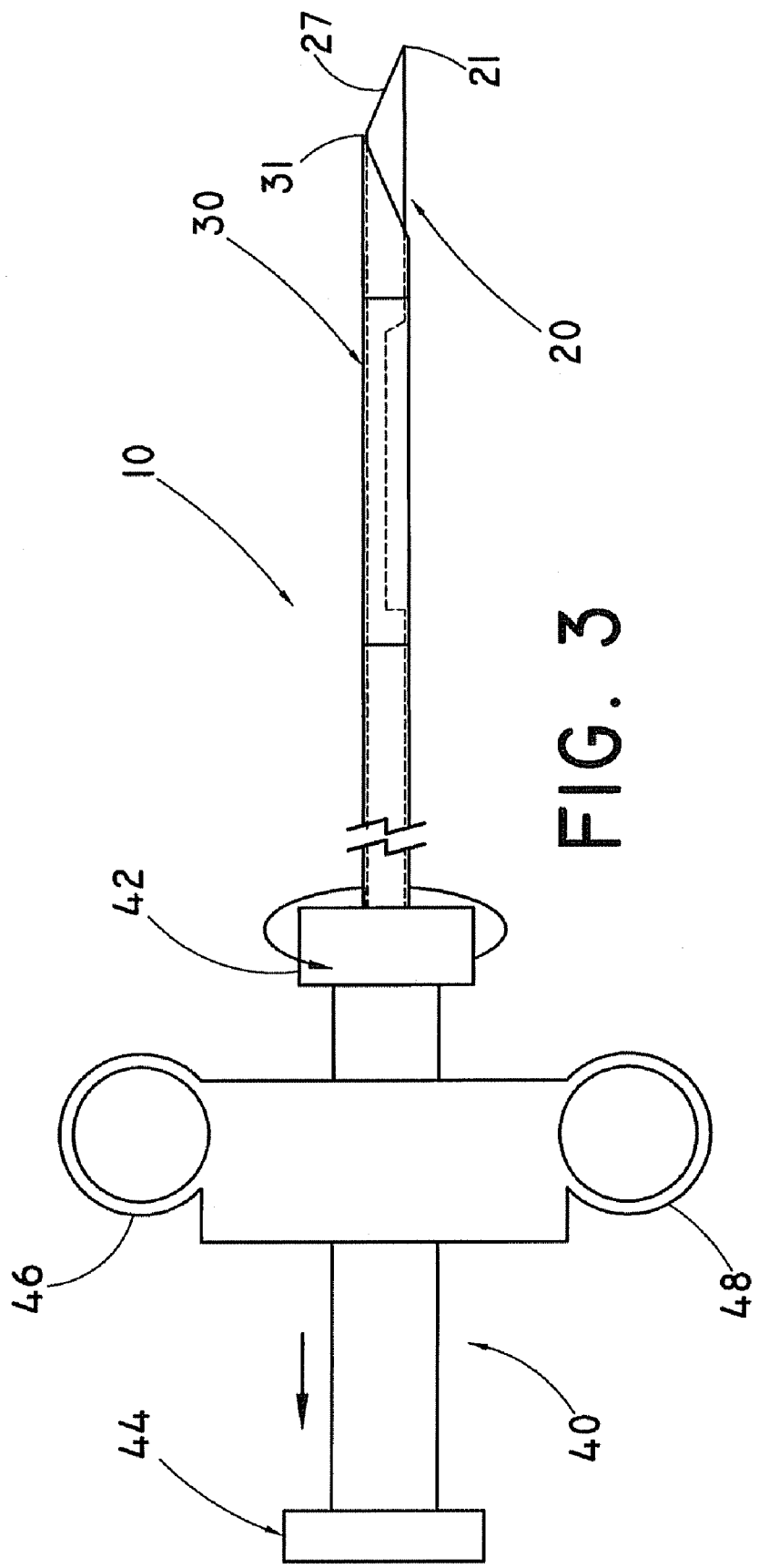
FIG. 3 is a plan view of the guidable cutting instrument of FIG. 2, following relative rotation of the respective stylet and outer cannula 180 degrees from the orientation of FIG. 2, resulting in the straightening of the distal end of the cutting instrument.

FIG. 3 is a plan view of the guidable cutting instrument of FIG. 2, following relative rotation of the respective stylet and outer cannula 180 degrees from the orientation of FIG. 2. As illustrated in FIG. 3, this relative rotation results in the straightening of the distal end of the cutting instrument 10 when compared to the curved, "in phase", configuration shown in FIG. 2.

FIG. 4 is a side view of one embodiment of a curved cannula 30 suitable for use in the guidable cutting instrument 10 of FIG. 2. As illustrated in FIG. 4, cannula 30 includes proximal and distal portions 32, 34, respectively. A hollow passageway (not shown) extends through cannula 30. As a non-limiting example, cannula 30 may be a stainless steel tube having a diameter of about 0.330 inch and a wall thickness between about 0.010 and 0.001 inch. Cannula 30 may also be constructed from any other suitable material including, but not limited to, metals, metal alloys such as nitinol, rigid or semi-rigid plastics, and composite materials. Cannulae, such as cannula 30, for use in biopsy cutting instruments are well known in the art (see, e.g., FIGS. 1 and 1A). Cannula 30 may be formed of virtually any composition and have any dimensions known to be appropriate in prior art non-curved cannulae, as long as the cannula is capable of selective curvature in combination with a stylet, as described herein. Those skilled in the art are readily able to select a particular cannula composition for use in a particular application.

As shown in FIG. 4, the distal portion 34 of cannula 30 comprises a shearing end 37 which terminates in a forward shearing tip 31. Preferably, shearing end 37 tapers in the distal direction to tip 31, as shown in the figure. More preferably, the shearing end comprises an annular, beveled edge about the distal portion 34 of cannula 30.

When in the normal configuration shown in FIG. 4, distal portion 34 of cannula 30 includes a curved segment. The curved segment may be formed in cannula 30 by methods well known in the art. Non-limiting examples of such methods include mechanical cold working/forming, and thermal setting of the material into the desired configuration. Distal portion 34 is provided at a gentle angle of curvature from the main body of cannula 30. Preferably, this angle is between about 5 and 45 degrees, and more preferably, about 10 degrees. The radius of curvature will preferably range between about 10 and 125 mm, and more preferably, about 60 mm. If desired, shearing end 37 may be formed of a different material than that of the main cannula body. In this event, shearing end 37 will generally will have a higher durometer (e.g., be harder) than the main body. For example, shearing end 37 can be formed of a material, such as a metal or metal alloy, having a relatively high hardness, and the main body of cannula 30 can be formed of a plastic having a lesser hardness. Shearing end 37 and distal portion 34 of the main cannula body can then be joined in any conventional manner, such as by adhesion.

FIG. 5 is a side view of the curved stylet 20 of the guidable cutting instrument 10 of FIG. 2. Stylet 20 is sized to be positioned within the hollow passageway of outer cannula 30, and is arranged for axial movement therein. As shown in FIG. 5, stylet 20 comprises proximal and distal portions 22, 24, respectively.

As a non-limiting example, stylet 20 may be stainless steel having a diameter of about 0.300 inch. The stylet may also be constructed from any other suitable material including, but not limited to, metals, metal alloys such as nitinol, rigid or semi-rigid plastics, and composite materials. Stylets, such as stylet 20, for use in biopsy cutting instruments are well known in the art (see, e.g., FIGS. 1 and 1A). Stylet 20 may be formed of virtually any composition and have any dimensions known to be appropriate in prior art non-curved stylets, as long as the stylet is capable of selective curvature as described herein, and is capable of slidable, yet snug, receipt in the interior passageway of cannula 30 as described. Those skilled in the art are readily able to select a particular stylet composition for use in a particular application.

As further shown in FIG. 5, stylet 20 comprises a recessed channel or notch 25 along the distal portion 24 of the stylet. In the embodiment shown, notch 25 comprises oppositely facing edges 26, 27. Edges 26, 27 may be formed at any angle or depth to enable specimen notch 25 to hold a tissue specimen of adequate size for use in a conventional examination, such as a biopsy.

Preferably, the specimen notch 25 has a length of up to about 3 to about 3.5 cm. More preferably, the notch has a length of about 1 cm to about 1.5 cm. Also, it is preferred that the notch 25 has a depth equal to about one half the stylet diameter. As further shown in FIG. 5, the stylet distal portion 24 comprises a tapered end 27 which terminates in a piercing distal tip 21. Preferably, the tapered end 27 comprises a tapered face having a cutting edge terminating in the forward piercing tip 21. However, this arrangement is not required, and the piercing end may alternatively be, e.g., cone-shaped. Formation of the notch 25 in the stylet may be accomplished in any conventional manner, such as by machining. Similarly, the stylet distal end tip may be sharpened by any conventional process, such as by grinding the tip in well-known fashion.

The respective angular portions of the stylet 20 and cannula 30 are selected and dimensioned in a manner such that when stylet 20 is positioned within the inner passageway of cannula 30, the distal end of the resulting cutting assembly 10 achieves a particular configuration resulting from the rotational alignment of the individual curves of the respective stylet 20 and cannula 30. Rotation of one of the stylet and cannula relative to the other enables the distal end of the needle assembly to be selectively maneuvered to a curved configuration when the respective curved distal ends are coincident with each other, or "in phase", as shown in FIG. 2.

Further rotation of either the stylet or cannula 180° relative to the other, maneuvers the respective curved distal ends "out of phase", or in other words, to the straight configuration as shown in FIG. 3. This configuration occurs due to the respective stylet and cannula curved ends cancelling each other out. Those skilled in the art will appreciate that the respective compositions and dimensions of each of stylet 20 and cannula 30 will be selected such that said cancellation is effected upon said out-of-phase rotation. Such selection is believed to be well-within the capability of those skilled in the art, and will not require more than routine experimentation.

The handle mechanism 40 permits relative movement, both axially and rotationally, between the stylet 20 and the cannula 30. Preferably, the handle mechanism includes an internal spring mechanism or other driver for permitting rapid axial movement of the cannula 30 over the stylet 20 in well known fashion, and/or for permitting axial movement of the stylet in the distal direction for sample collection purposes, as exhibited in conventional needle assemblies. Spring-loaded handle mechanisms permitting such relative movement are known in the art and are described, for example, in U.S. Pat. No. 5,538, 010 and U.S. Patent Publication No. 2004/0133124 A1. Other examples of spring-loaded handles are shown, e.g., in U.S. Pat. Nos. 4,958,625 and 5,195,533. All patent documents cited herein are incorporated by reference in their entirety.

In the non-limiting embodiment shown, handle mechanism 40 includes a trigger 44, as well as finger grips 46, 48. Handle mechanism 40 is provided with a dial 42 or a functionally similar feature for permitting relative rotation between stylet 20 and cannula 30. Preferably, cannula 30 is rotationally engaged with dial 42 in a manner such that rotation of dial 42 by the operator causes a corresponding rotation of cannula 30. This arrangement can be accomplished in any conventional fashion, such as by joining the dial and cannula via the injection molding of the dial to the cannula, or by joining the components by way of an adhesive, such as an epoxy binder. In this arrangement, stylet 20 is not rotationally engaged with dial 42 and cannula 30, and as a result, stylet 20 does not rotate upon rotation of dial 42 and cannula 30.

Typically, stylet 20 is fastened to handle/lever 44, and thereby, held from rotation. With minor modification, the relative rotation can be reversed from that described above. In this event, stylet 20 is rotatable, and outer cannula 30 is in a fixed, or non-rotatable, condition.

The selective manipulation of the distal end 11 of the guidable cutting instrument 10 between the curved, in phase, configuration, and the straight, out of phase, configuration enables the physician to selectively alter the configuration of the distal end of the cutting instrument, and thereby avoid obstructions as the cutting instrument is advanced into the body of a patient under real time visualization. In this manner, the physician can navigate the cutting instrument around the obstructions, and access a target tissue sample for removal without penetrating body organs or other impediments encountered within the body. At the same time, the cutting instrument retains the ability for the cannula 30 to move smoothly and freely over stylet 20 to sever a tissue specimen, thereby causing the sample to be captured in the notch. Such movement can occur in either the curved alignment of the stylet 20 and cannula 30 as shown in FIG. 2, or the straight alignment of the stylet and the cannula as shown in FIG. 3. It is preferred that this movement occur in the curved position, as it is believed that this arrangement reduces drag between the stylet and cannula. This action facilitates rapid advancement of the outer cannula over the stylet. The faster the advancement, the better likelihood that the targeted tissue sample will be captured in the notch.

During use of the inventive cutting instrument 10 for obtaining a tissue sample, the distal end of the cutting instrument 10 is initially percutaneously inserted into the body of the patient in conventional manner, and under real time visualization. It is anticipated that ultrasound visualization will be the preferred manner of visualization. However, any other methods of visualization that are capable of providing suitable images may also be utilized. At the time of insertion, the distal end of the cutting instrument will be in either the curved configuration of FIG. 2, or the straight configuration of FIG. 3. The particular configuration selected will be derived from the particular image received from the UV monitor.

If the distal end is inserted, for example, in the straight configuration, the physician will advance the distal end of the cutting instrument under visualization until an obstruction, such as a body organ, is observed in the path of the needle. At this time, the physician may rotate dial 42 up to 180°, thereby manipulating the distal end of cutting instrument 10 up to the fully curved configuration illustrated in FIG. 2 (resulting from the 180° rotation), or to any curved configuration between the respective configurations of FIGS. 2 and 3 (resulting from a rotation less than 180°). In this fashion, the distal end of the instrument can be steered around the obstruction. Further manipulation in this fashion can be carried out to avoid additional obstructions, or to straighten the distal end following a successful navigation around an obstruction.

Once the distal end of the cutting instrument has reached the target tissue, the needle may be activated in conventional fashion to sever the tissue sample of interest. For example, the handle may be activated such that stylet 20 is initially advanced beyond the distal end of the cannula 30 into the targeted tissue mass, wherein a segment of the tissue mass is prolapsed into the specimen-receiving notch 25 of the stylet. The handle trigger 44 is then activated to rapidly advance the cannula over the stylet. This action of the cannula severs the tissue sample, and captures the sample in the notch. The cutting instrument having the sample captured therein is then retracted from the body. Depending upon the anatomy at the location at which the biopsy sample is severed, it may be necessary to manipulate or navigate the needle upon removal in a generally reverse fashion when compared to the insertion method, in order to avoid obstructions. Following removal, the cannula is retracted, and the sample is recovered from the stylet notch for further examination.

Those skilled in the art will appreciate that the above-described guidable cutting instrument is merely one illustrative embodiment of the principles of this invention and that other cutting instruments may be devised without departing from the spirit and scope of this invention. For example, the distal end of the cannula 30 may be devised to include serrated teeth or a modified cutting edge for providing any number of different cutting or slicing actions. As another example, the distal end of stylet 20 may be devised to achieve any number of different piercing actions.

While these features have been disclosed in connection with the illustrated preferred embodiments, other embodiments of the invention will be apparent to those skilled in the art that come within the spirit of the invention as defined in the following claims.

The invention claimed is:

1. A guidable cutting instrument for use in cutting a tissue specimen from a tissue mass, comprising:
    a cannula having a proximal portion and a distal portion, said distal portion having a curve formed therealong;
    a stylet having a proximal portion and a distal portion, said stylet distal portion having a specimen-receiving notch formed therein and having a curve formed therealong, said stylet received in said cannula and axially extendable therefrom such that said notch is capable of penetrating said tissue mass, said cannula being axially movable over said extended stylet for severing said tissue specimen from said mass for capture in said notch, said cannula and said stylet being structured and arranged for relative rotation between a first position wherein said cannula curve and said stylet curve are in phase and said respective curves coincide to define a curved condition for a length of said cutting instrument, and a second position wherein said cannula curve is rotated relative to said stylet curve in a manner to define a generally linear condition of said cutting instrument; and
    a handle structured for driving relative axial and rotational movement between said cannula and said stylet, said handle engaged with a proximal end of said cannula proximal portion for effecting said axial movement of said cannula over said extended stylet, said handle comprising a trigger, a plurality of finger grips, and a dial positioned distal of said finger grips, said dial engaged with the proximal end of said cannula for effecting said relative rotation between said cannula and said stylet.

2. The guidable cutting instrument of claim 1, wherein said handle is structured for effecting said axial extension of said stylet.

3. The guidable cutting instrument of claim 1, wherein said handle comprises a driver for effecting said axial movement of said cannula.

4. The guidable cutting instrument of claim 1, wherein said cannula is capable of a rotation of 180 degrees from said first position to said second position.

5. The guidable cutting instrument of claim 1, wherein the cannula further comprises a shearing distal end.

6. The guidable cutting instrument of claim 5, wherein said shearing distal end of said cannula is formed from a composition having a higher durometer than a durometer of a main body portion of said cannula.

7. The guidable cutting instrument of claim 6, wherein said cannula shearing distal end is formed of a metal or a metal alloy, and said main body portion is formed of a plastic.

8. A method of retrieving a tissue specimen from a tissue mass of a patient, comprising:
    inserting a distal end of a tissue-penetrating cutting instrument into an interior space of the body of the patient, said tissue-penetrating cutting instrument comprising a cannula having a proximal portion and a distal portion, said distal portion having a curve formed therealong; a stylet having a proximal portion and a distal portion, said stylet distal portion having a specimen-receiving notch formed therein and having a curve formed therealong, wherein said stylet is received in said cannula and axially extendable therefrom, and said cannula is axially extendable over said extended stylet, said cannula and said stylet being structured and arranged for relative rotation between a first position wherein said cannula curve and said stylet curve are in phase and said respective curves coincide in a manner to define a curved condition for a distal portion of said cutting instrument, and a second position wherein said cannula curve is rotated relative to the stylet curve in a manner to define a generally linear condition of said cutting instrument; and a handle engaged with a proximal end of said cannula proximal portion for effecting said axial extension over said stylet, said handle comprising a trigger, a plurality of finger grips, and a dial positioned distal of said finger grips, said dial engaged with the proximal end of said cannula for effecting said relative rotation between said cannula and said stylet;
    navigating said interior space under real time visualization such that said cutting instrument distal end approaches the tissue mass, said navigating step including rotating said dial for effecting said relative rotation of said cannula and stylet between said first position and said second position for traversing obstructions encountered in said interior space;
    advancing said stylet such that said notch extends beyond said cannula and penetrates said tissue mass;
    advancing said cannula over said notch to sever said specimen from said tissue mass and to capture said severed specimen in said notch; and
    withdrawing said cutting instrument, and retrieving said specimen from said notch.

9. The method of claim 8, wherein said navigating step is carried out under ultrasonic visualization.

10. The method of claim 8, wherein said withdrawing step comprises navigating said interior space under real time visualization.

11. The method of claim 8, wherein said trigger is operationally engaged with said cannula for advancing said cannula over said stylet notch for severing said specimen.

12. A guidable cutting instrument for use in cutting a tissue specimen from a tissue mass of a patient, comprising:
    a cannula having a proximal portion and a distal portion, said distal portion having a curve formed therealong and having a shearing distal end, said shearing distal end terminating in a shearing distal tip, said shearing distal end formed of a material having a higher durometer than a material of a main body portion of said cannula, said distal portion having an angle of curvature of between about 5 and 45 degrees;
    a stylet having a proximal portion and a distal portion, said stylet distal portion having a curve formed therealong and having a specimen-receiving notch formed along said curve, said stylet distal portion having a tapered distal end terminating in a piercing distal tip, said stylet received in said cannula and axially extendable therefrom such that said notch is capable of penetrating said tissue mass, said cannula being axially movable over said extended stylet for severing said tissue specimen from said mass for capture in said notch, said cannula and said stylet being structured and arranged for relative rotation between a first position wherein said cannula curve and said stylet curve are in phase and said respective curves coincide to define a curved condition for a length of said cutting instrument, and a second position wherein said cannula is rotated relative to said stylet in a manner to define a generally linear condition of said cutting instrument; and a handle engaged with a proximal end of said cannula proximal portion for effecting said axial movement of said cannula over said extended stylet, said cannula capable of said axial movement over said stylet in both said first and said second positions, said handle comprising a trigger, a plurality of finger grips, and a dial engaged with said cannula proximal end, said dial positioned distal of said finger grips and permitting a rotation of said cannula of 180 degrees from said first position to said second position, said stylet non-rotatably engaged with said handle.

13. The guidable cutting instrument of claim 12, wherein said angle of curvature is about 10 degrees.

* * * * *